United States Patent [19]

Hayden et al.

[11] Patent Number: 5,387,751
[45] Date of Patent: Feb. 7, 1995

[54] PRODUCTION OF OLEFINE OXIDES

[75] Inventors: Percy Hayden; Richard W. Clayton; John R. Ramforth, all of Middlesbrough, England; Alan F. G. Cope, Cheltenham, Australia

[73] Assignee: Imperial Chemical Industries PLC, London, England

[21] Appl. No.: 100,338

[22] Filed: Aug. 2, 1993

Related U.S. Application Data

[63] Continuation of Ser. No. 915,872, Jul. 20, 1992, abandoned, which is a continuation of Ser. No. 733,968, Jul. 22, 1991, abandoned, which is a continuation of Ser. No. 555,827, Jul. 23, 1990, abandoned, which is a continuation of Ser. No. 205,500, Jun. 10, 1988, abandoned, which is a continuation of Ser. No. 591,183, Mar. 19, 1984, abandoned, which is a continuation of Ser. No. 429,424, Sep. 30, 1982, abandoned.

[30] Foreign Application Priority Data

Feb. 10, 1978 [GB] United Kingdom ............ 5439
Mar. 20, 1978 [GB] United Kingdom ............ 10940

[51] Int. Cl.$^6$ ............................................. C07D 301/10
[52] U.S. Cl. ..................................... 549/534; 549/536
[58] Field of Search ............................. 549/534, 536

[56] References Cited

U.S. PATENT DOCUMENTS

| | | | |
|---|---|---|---|
| 2,279,469 | 4/1942 | Law et al. | 529/534 |
| 2,279,470 | 4/1942 | Law et al. | 549/534 |
| 2,479,883 | 8/1949 | West et al. | 252/416 |
| 2,479,884 | 8/1949 | West et al. | 549/534 |
| 2,479,885 | 8/1949 | West et al. | 252/415 |
| 2,687,380 | 8/1954 | Saffer | 252/411 |
| 2,963,444 | 12/1960 | Nixon | 252/416 |
| 4,007,135 | 2/1977 | Hayden et al. | 252/467 |
| 4,012,425 | 3/1977 | Nielsen et al. | 549/534 |
| 4,051,608 | 9/1977 | Rebsdat | 252/412 |
| 4,066,575 | 1/1978 | Winnick | 252/475 |
| 4,094,889 | 6/1978 | Hayden et al. | 549/534 |
| 4,168,247 | 9/1979 | Hayden et al. | 252/476 |
| 4,177,169 | 12/1979 | Rebsdat et al. | 252/476 |
| 4,207,210 | 6/1980 | Kilty | 252/463 |
| 4,226,782 | 10/1980 | Hayden et al. | 549/534 |

FOREIGN PATENT DOCUMENTS

| | | | |
|---|---|---|---|
| 488990 | 12/1952 | Canada | 549/536 |
| 1138941 | 2/1957 | France . | |
| 524007 | 7/1940 | United Kingdom | 549/534 |
| 1369640 | 10/1974 | United Kingdom . | |
| 1515514 | 6/1978 | United Kingdom . | |
| 1517608 | 7/1978 | United Kingdom . | |

Primary Examiner—C. Warren Ivy
Assistant Examiner—Ba K. Trinh
Attorney, Agent, or Firm—Cushman Darby & Cushman

[57] ABSTRACT

Olefine oxides are produced by contacting an olefine with oxygen in the presence of a silver containing catalyst and a chlorine-containing reaction modifier; the performance of the catalyst is improved by contacting it with a nitrate or nitrite forming substance for example nitric oxide.

5 Claims, No Drawings

PRODUCTION OF OLEFINE OXIDES

This is a continuation of application Ser. No. 07/915,872, filed Jul. 20, 1992 which is an con of 07/733,968 filed Jul. 22, 1991 which is an con of 07/555,827, filed Jul. 23, 1990 which is an con of 07/205,500 filed Jun. 10, 1988 which is an con of 06/51,183, filed Mar. 19, 1984 which is an con of 06/429,424, filed Sep. 30, 1982, all now abandoned.

THIS INVENTION relates to the production of olefine oxides.

The invention comprises a process of producing an olefine oxide which comprises contacting an olefine for example propylene or preferably ethylene with oxygen in the presence of a silver-containing catalyst and a chlorine-containing reaction modifier in which the performance of the catalyst is improved, for example in that the selectivity of the catalyst is improved or at least partly maintained or restored, by contacting the catalyst also with a nitrate or nitrite forming substance which is in a gas phase.

The invention also comprises a process of producing an olefine oxide which comprises contacting an olefine for example propylene or preferably ethylene with oxygen in the presence of a silver-containing catalyst and a chlorine-containing reaction modifier in which the performance of the catalyst is improved, for example in that the selectivity of the catalyst is improved or at least partly maintained or restored, by contacting the catalyst with a gas comprising $N_2O_4$ and/or $NO_2$ or a nitrogen containing compound together with an oxidising agent which is preferably oxygen.

The nitrogen containing compound may be an organic nitrogen containing compound or a compound of nitrogen with hydrogen and/or oxygen. Such compounds are believed to function by forming nitrate and/or nitrite ions in the catalyst. The presence of such ions in the catalyst may be determined by extracting the catalyst with water and analysing the solution produced thereby.

By the selectivity of the catalyst is meant the proportion of the olefine consumed which is converted to an olefine oxide in the process. The selectivity of silver-containing catalysts in the process may fall with prolonged use. We have found that contacting used catalyst with a nitrate or nitrite forming substance tends to improve or at least partly to restore the selectivity of the catalyst, and continuously contacting the catalyst with a nitrate or nitrite forming substance in the process in general maintains the selectivity of the catalyst or reduces the rate of loss of selectivity of the catalyst. Restoration Of the selectivity of the catalyst may be carried out more than once if desired.

By a nitrate or nitrite forming substance is meant a compound which is capable under the conditions in which it is contacted with the catalyst of introducing nitrate or nitrite ions to the catalyst. The preferred nitrate or nitrite forming substances are nitric oxide and oxygen, nitrogen dioxide and/or dinitrogen tetroxide. Hydrazine, hydroxylamine or ammonia together with oxygen may be used.

Organic compounds capable on oxidation of producing nitrate or nitrite ions in the catalyst may be used together with an oxidising agent which is preferably oxygen; for example esters of nitrous acid for example methyl nitrite, nitroso compounds for example N-nitroso compounds, nitroso butane, organic nitro compounds especially the nitro paraffins having 1-4 carbon atoms for example nitromethane, nitroaromatic compounds, especially nitrobenzene, and N-nitro compounds, nitriles, for example acetonitrile, HCN, amides for example formamide or amines for example $C_1$ to $C_4$ alkylamines especially methylamine or ethylene diamine may be used.

The catalyst suitably comprises silver supported on a porous heat resisting support which has a specific surface area in the range 0.05 to 10 $m^2/g$ and preferably 0.1 to 5 $m^2/g$ and more preferably 0.3 to 5 $m^2/g$ as measured by the Brunauer, Emmett and Teller method.

The support is suitably a preformed support.

The silver may be introduced to a preformed porous heat resisting support as a suspension of silver or silver oxide in a liquid medium for example water or by impregnation of the support with a solution of a silver compound which can be reduced to silver metal if necessary by means of a reducing agent for example hydrogen. If necessary a heat treatment may be used to decompose the silver compound to silver. Suitably the impregnating solution contains a reducing agent which may be for example an anion, for example a formate, acetate, propionate, lactate, oxalate or tartarate ion, of a silver compound in the solution. The reducing agent may be for example an aldehyde, for example formaldehyde or acetaldehyde or an alcohol preferably having 1 to 4 carbon atoms for example methanol or ethanol.

The solution may be a solution in water and/or an organic solvent, for example an aliphatic alcohol preferably having 1 to 4 carbon atoms; a polyhydric alcohol for example ethylene glycol or glycerol; a ketone for example acetone; an ether for example dioxan or tetrahydrofuran; a carboxylic acid for example acetic acid or preferably molten lactic acid which is preferably used in the presence of water and suitably in the presence of an oxidising agent for example $H_2O_2$; or an ester for example ethyl acetate or a nitrogen containing base for example pyridine or formamide. An organic solvent may function as a reducing agent and/or complexing agent for the silver also.

If the silver is introduced by impregnating a support with a solution of a decomposable silver compound it is preferred that ammonia and/or a nitrogen containing base should be present. The nitrogen containing base suitably acts as a ligand maintaining the silver in solution; for example it may be pyridine, acetonitrile, an amine, especially a primary or secondary amine having 1-6 carbon atoms, or preferably ammonia. Other suitable nitrogen-containing bases include acrylonitrile, hydroxyamine and alkanolamines for example ethanolamine, alkylene diamines having from 2-4 carbon atoms or polyamines containing at least three carbon atoms for example diethylenetriamine or amino ethers with at least one ether linkage and at least one primary or secondary amino group e.g. morpholine or amides for example formamide or dimethyl formamide. The nitrogen-containing bases may be used alone or in admixture. They also act as reducing agents for the silver compound. Suitably the nitrogen containing base or bases are used together with water.

Alternatively the solution may be a neutral or acid solution for example it may be a solution of a silver carboxylate especially a formate, acetate, propionate, oxalate, citrate, tartarate or preferably lactate or for example a solution of silver nitrate.

The solutions preferably contain 3-50% of silver by weight.

impregnation may be carried out in a single stage or if desired may be repeated one or more times. By this means higher silver contents of the catalyst may be achieved.

The silver compound may be decomposed for example in an atmosphere of air or nitrogen.

The silver compound may generally be partially or completely reduced to silver by heating in the range 100° to 350° C., for example for a period of 5 mins to 4 hours: alternatively reduction may be carried out during the oxidation of the olefine to the olefine oxide.

The catalyst support preferably has apparent porosity as measured by the mercury absorption method of at least 20%, for example 30–80% preferably 30–65% and more preferably 40–60% and mean pore diameters of 0.1 to 20 microns preferably 0.3 to 4 microns as measured by the mercury porosimetry method. The pore size distribution of the support may be bimodal, in which case the smaller pores preferably account for at least 70% of the total pore volume and have a mean pore diameter preferably in the range of 0.1 and preferably 0.3 to 4 microns, end the larger pores preferably have a mean pore diameter in the range 25 to 500 microns.

Most of the silver content of the catalyst is preferably present in the form of discrete particles adhering to the support having equivalent diameters of less than 10,000 Å preferably in the range 20–10,000 Å and more preferably 40–8,000 Å for example 100–5,000 Å. By equivalent diameter is meant the diameter of a sphere of the same silver content as the particle.

Preferably at least 80% of the silver is present as particles having equivalent diameters in the aforesaid range, the quantity of silver being judged in terms of the number of particles falling in that range. The silver is believed to be present largely as metallic silver. The dimensions of the silver particles may be determined by scanning electron microscopy.

The support may be an alumina, silicon carbide, silica, zirconia, titania or silica/alumina support, but it is preferably composed of an aggregate of alpha-albumina particles which may be fused together or cemented together with, for example silica or baryta.

The catalyst preferably comprises 3 to 50% and more preferably 3 to 30% for example 6 to 28% by weight of silver.

It is preferred that the catalyst should contain cations, for example alkali and/or alkaline earth metal cations as the corresponding nitrate or nitrite or in a form capable of reacting to produce the corresponding nitrate or nitrite. This is especially preferred if the catalyst is treated with the nitrate or nitrite forming substance intermittently in order to restore its selectivity. It is believed that an effect of such cations is to hold more nitrate and/or nitrite ions on the catalyst or to hold them longer than is the case in their absence but we do not wish to be bound by any theory as to their action.

The cations may be introduced to the support before during or after the introduction of the silver compound. Preferably the cations are introduced to a support in which the silver is present in metallic form. The cations are suitably introduced as solutions in water and/or organic solvents. If it is desired to impregnate a catalyst which has already been used in the oxidation of an alkene to an alkylene oxide and has lost performance, this may be carried out also. Suitable concentrations of such cations in a form which is extractable by water may be for example $5 \times 10^{-5}$ to 2 and preferably $5 \times 10^{-4}$ to 2 and more preferably $5 \times 10^{-4}$ to 0.5 gram equivalents per kilogram of catalyst.

The cations are preferably provided as nitrates, hydroxides, carbonates, bicarbonates or carboxylates.

The catalyst preferably contains (a) molybdenum and/or more preferably rubidium and/or cesium and/or (b) lithium, cadmium, calcium, strontium and/or barium and/or more preferably sodium and/or potassium, these elements being present as compounds which are extractable from the catalyst by water; preferably at least one element of both (a) and (b) is present in this form.

Suitably, Mo, K, Sr, Ca and/or barium are present in amounts of 2 to 20,000, and preferably 2 to 10,000 and more preferably 10 to 3000 $\mu$ gram equivalents per gram of silver; cesium, rubidium and/or molybdenum in amounts of KS $\mu$ gram equivalents per gram of catalyst where K is 0.1 to 60 for example 0.5 to 30 and preferably 1 to 20 and more preferably 1 to 12 and S is the surface area of the catalyst in square meters per gram.

Partial pressures of ethylene or propylene in processes according to the invention may be in the ranges 0.1–30 and preferably 1 to 30 bars. The total pressure may be in the range of from 1 to 100 and preferably 3–100 bars absolute. The molar ratio of oxygen to ethylene or propylene may be in the range 0.05 to 100. The partial pressure of oxygen may be in the range 0.01 and preferably 0.1 to 20 bars and preferably 1–10 bars. The oxygen may be supplied for example in the form of air or preferably as commercial oxygen. A diluent for example helium, nitrogen, argon, carbon dioxide and/or a lower paraffin for example ethane and/or preferably methane may be present in proportions of 10–80% and preferably 40–70% by volume in total. Suitably the diluent comprises methane as aforesaid together with, for example 100 to 100,000 parts per million by volume of ethane, preferably together with small amounts, for example 10 to 10,000 parts per million by volume of $C_3$ to $C_6$ alkanes, cycloalkanes or alkenes preferably propylene, cyclopropane, isobutene or isobutane. It is necessary to operate using gas compositions which are outside the explosive limits.

The temperature is suitably in the range 180° to 320° C., preferably 200° to 300° C. and more preferably in the range 220° to 290° C. Contact times should be sufficient to convert 0.5–70%, for example 2 to 20 and preferably 5–20% of the ethylene or propylene and unconverted ethylene or propylene is, after separation of the product, suitably recycled, optionally in the presence of unconverted oxygen where appropriate and suitably after removal of $CO_2$.

Suitable catalysts for use in this invention and process conditions may be as described in our copending British Patent Application No. 21612/77, and in our British Patent Applications Nos. 22286/76 and 21611/77 (equivalent to Netherlands patent applications 7705847 and 7805163 and U.S. application Ser. Nos. 796068 and 903403)

The chlorine-containing reaction modifier may be of known type. It is preferred that it should be a $C_1$ to $C_{10}$ compound also containing hydrogen. It may be for example 1,1 or preferably, 1,2-dichlorethane but it is preferred to use methyl chloride or more preferably vinyl chloride. Chlorinated aromatic compounds, for example chlorobenzene, dichlorobenzene and chlorinated toluenes are also suitable. It is preferred that the concentration of the chlorine containing reaction modifier should be in the range 0.1–500 and preferably 1 to 50 parts per million parts of the reaction medium by weight.

The nitrate or nitrite forming substance may be supplied continuously to the process at a low level for example 0.1 and preferably 0.2 to 200 and preferably 0.5 to 50 parts per million of $NO_2$ equivalent of the process gas by volume. If desired the whole of the gas contacting the catalyst may consist of the nitrate or nitrite forming substance though it is of course necessary in the case of substances requiring oxidation to ensure that sufficient oxygen is present either by pre- or post oxidation of the catalyst or in the gas to allow the production of nitrate or nitrite. Preferably the gas is flowed through the catalyst. Not all substances have the same efficiency in forming nitrate or nitrite ions in the catalyst. By $NO_2$ equivalent is meant the amount of the substance which is equivalent to the specified amounts of $NO_2$. In general one mole of NO, 0.5 moles of $N_2O_4$, and under typical conditions about ten moles of ammonia, three moles of ethylene diamine and two moles of acetonitrile are equivalent to one mole of $NO_2$. The values must however be determined experimentally for each compound under the appropriate conditions either by determining the amount equivalent to the desired amount of $NO_2$ under operating conditions or (less suitably) by determining the quantity of $NO_3$ ions deposited on a catalyst bed under standard conditions compared with the quantity deposited by $NO_2$.

Improvement or restoration of the selectivity of a catalyst which has lost selectivity in the reaction may be carried out at a wide range of temperatures for example from 20° C. to 350° C. but temperatures of 150°–300° C. are preferred. The pressures may be in the range 0.1 to 100 bars but are preferably in the range 1–50 bars absolute.

Suitably in regeneration of the catalyst at least 50 and preferably at least 300 parts of nitrate and/or nitrite per million parts by weight of the catalyst are added.

Regeneration may be carried out in the presence of the reactants and under normal reaction conditions by introducing the nitrate or nitrite forming compound to the reaction and preferably maintaining in the catalyst a concentration of at least 50 and more preferably at least 300 parts of nitrate and/or nitrite per million parts by weight of catalyst, The catalyst may be in a fluidised or preferably a fixed bed suitably packed in an appropriately dimensioned tubular reactor.

EXAMPLE 1

Catalysts for the oxidation of ethylene to ethylene oxide were prepared as follows:

10.4 g of reagent grade silver acetate were dissolved in the minimum amount of ammonia solution required to give complete dissolution. This solution was then filtered and the filtrate made up to 12 ml with water. A support material (60 g), alpha-alumina composite sold by Norton Co. under the trade mark ALUNDUM, was impregnated with the silver solution. The surface area of the support material was 0.3 m²/g, the mean pore diameter was 2.8 microns and the water porosity was 20%. The support was in the form of particles with diameters in the range 0.42–1 mm. The support impregnated with the silver solution was heated in a forced draught oven at 290° C. for a period of 3 hours. This procedure results in a catalyst containing about 8% silver by weight. This catalyst was then promoted with alkali metal nitrates using the following technique:

Appropriate amounts of sodium nitrate and potassium nitrate or rubidium nitrate were dissolved in 4 ml of water. This solution was used to impregnate 20 g of the supported silver catalyst. The impregnated catalyst was then dried at 120° C. for 1 hour in a forced draught oven.

Three alkalised catalysts A, B and C were prepared in this way. The alkali metal contents, expressed in parts per million by weight, are given in Table 1.

EXAMPLE 2

The catalysts prepared in Example 1 were tested in the following way:

20 g of catalyst was loaded into a stainless steel reactor. The catalyst was heated up to 240° C. under a stream of nitrogen and then a process gas stream was introduced at a pressure of 225 pounds per square inch gauge. The process gas stream contained 30% ethylene, 8% oxygen, 10 ppm vinyl chloride, 3 ppm nitric oxide and 62% nitrogen. The catalyst selectivities and percentage conversion of oxygen were measured after a period of 2 weeks at a gas hourly space velocity of 3,000 $hr^{-1}$. The results obtained from catalysts A, B and C are shown in Table 1.

TABLE 1

| Catalyst | Na Concen. (ppm) | K Concen. (ppm) | Rb Concen. (ppm) | Selectivity | Oxygen Conversion (%) |
| --- | --- | --- | --- | --- | --- |
| A | 200 | — | 30 | 90 | 10 |
| B | 200 | — | 100 | 92 | 10 |
| C | 200 | 130 | — | 86 | 7 |

EXAMPLE 3

A catalyst for the oxidation of ethylene to ethylene oxide was prepared as follows:

30 g of reagent grade silver acetate was dissolved into 30 ml of aqueous ammonia (S.G. 0.880) and the solution was filtered. 7.2 ml of a solution containing 8.9 g sodium acetate in 20 ml distilled water and 3.6 ml of a solution containing 1.68 g rubidium carbonate in 250 ml distilled water were added to the silver acetate solution. All of this solution was used to impregnate 180 g of the support material. The support material was an alpha-alumina composite sold by Norton Co. under the trade mark ALUNDUM which had previously been crushed and sieved to give particles with diameters in the range 0.42–1 mm. The surface area of the support material was 0.3 m²/g, the mean pore diameter was 2.8 microns and the water porosity was 20%.

The support impregnated with the silver solution was heated in a forced draught oven for 3 hours at 290° C. The procedure resulted in a catalyst containing 8% silver, 0.3% sodium, and 0.01% rubidium all by weight.

The catalyst was tested in the following way:

20 g of the catalyst was loaded into a stainless steel reactor (internal diameter 8 mm) contained in a thermostatically controlled fluidised sand bath. The catalyst was heated to 240° C. over a period of about 40 minutes in a stream of nitrogen at a gas hourly space velocity of 3000 $hr^{-1}$ and a pressure of 240 p.s.i.a. When the reaction temperature had been achieved, the nitrogen feed was stopped and the process gas mixture introduced to the reactor. The process gas contained 30% ethylene, 8% oxygen and 10 ppm vinyl chloride, the balance being nitrogen, at a pressure of 240 p.s.i.a. and a GHSV of 3000 $hr^{-1}$. After stabilisation the selectivity was 93% and the oxygen conversion 5%. The catalyst was allowed to react under these conditions until it gave a selectivity of 87% to ethylene oxide at 5% oxygen conversion.

At this point the flow of process gas was stopped and the nitrogen supply was reintroduced to the reactor, and this supply was adjusted until a GHSV of 400 hr$^{-1}$ was achieved at 30 p.s.i.a. With the reactor temperature maintained at 240° C., a stream containing 0.8% nitric oxide and 8% oxygen in helium was passed over the catalyst for 3 hours at 30 p.s.i.a. and a GHSV of 400 hr$^{-1}$. Following this treatment the nitrogen supply was reintroduced to the reactor at 30 p.s.i.a. and a GHSV of 4000 hr$^{-1}$ and this feed was adjusted until a pressure of 240 p.s.i.a. was achieved at a GHSV of 3000 hr$^{-1}$. The process gas mixture as previously described was then introduced to the reactor at a GHSV of 3000 hr$^{-1}$ and 240 p.s.i.a. After the catalyst performance had stabilised, a selectivity of 94% to ethylene oxide at 5% oxygen conversion was achieved.

GHSV means gas hourly space velocity p.s.i.a. means pounds per square inch absolute.

By oxygen conversion is meant the percentage of the oxygen which is fed which is consumed.

EXAMPLE 4

A catalyst for the oxidation of ethylene to ethylene oxide was prepared as follows:

30 g of reagent grade silver acetate was dissolved into 30 mls of aqueous ammonia (SG 0.880) and the solution was filtered. This solution was used to impregnate 180 g of support material. The support material was an alpha-alumia composite sold by Norton Co. under the trade mark ALUNDUM which had previously been crushed and sieved to give particles with diameters in the range 0.42–1 mm. The surface area of the support material was 0.3 m$^2$/g; the mean pore diameter was 2.8 microns and the water porosity was 20%.

The support impregnated with the silver solution was heated in a forced draught oven for 3 hours at 290° C. The procedure resulted in a catalyst containing 8% silver.

The catalyst was tested in the following way:

10 g of the catalyst was loaded into a glass U-tube reactor of diameter 10 mm. The catalyst was heated to 240° C. in a stream of nitrogen at a GHSV of 800 hr$^{-1}$ and a pressure of 20 p.s.i.a. When the reaction temperature had been achieved, the flow of nitrogen was adjusted and the process gases were introduced. The process gas contained 30% ethylene, 8% oxygen 10 ppm vinyl chloride and 5 ppm nitric oxide in nitrogen at a pressure of 20 p.s.i.a. and a GHSV of 800 hr$^{-1}$. After the catalyst performance had stabilised a selectivity of 87% to ethylene oxide was achieved at an oxygen conversion of 8%.

When the above example was repeated with a process gas containing no nitric oxide a selectivity of 85% to ethylene oxide was achieved at an oxygen conversion of 8%.

EXAMPLE 5

Catalysts 1–8 for the oxidation of ethylene to ethylene oxide were prepared as follows:

80 g of ammonium oxalate was dissolved in 2.5 l. of water. To this solution a solution of silver nitrate (100 g AgNO$_3$ in 250 ml water) was added. The precipitate of silver oxalate was filtered, washed with cold water and dried at room temperature under vacuum.

4.8 g of silver oxalate, together with appropriate amounts of sodium nitrate and rubidium nitrate were dissolved in 12.5 ml of a solvent which contained 40% ethylene diamine, 50% water and 10% ethanolamine. The addition of the silver oxalate was carried out slowly to avoid overheating the solution. This solution was used to impregnate 25 g of the support material. The support material used was an alpha-alumina composite sold by the Carborundum Co. The surface area of the support material was 0.6 m$^2$/g, the mean pore diameter was 2.3 $\mu$ and the water porosity was 50%. The support was in the form of particles with diameters in the range 0.42–1 mm. The support impregnated with the silver solution was heated in a nitrogen atomosphere at a temperature of 200° C. for a period of 1 hour.

The final catalysts contain about 12% by weight of silver. The levels of sodium and rubidium present enpressed in parts per million by weight, are given in Table 2.

EXAMPLE 6

Catalysts 9–12 for the oxidation of ethylene to ethylene oxide were prepared as follows:

9.3 g of silver oxalate, prepared by the method described in Example 5, were dissolved in 16.2 ml of a 50:50 v/v solution of ethylene diamine in water. To this solution 1.8 ml of ethanolamine was added. 30 g of the support material was then stirred into the silver solution and the mixture left to stand for about 10 mins. The excess solution was then drained from the support and the resulting damp solid was heated under nitrogen in a forced draught oven for a period of 1 hour at a temperature of 200° C. The support was supplied by Norton Co. under the trade mark ALUNDUM. It was an alpha-alumina composite which had been crushed and sieved to give particles with diameters in the range 0.42–1 mm. The surface area of the support material was 0.3 m$^2$/g, the mean pore diameter was 2.8 microns and the water porosity was 20%. The resulting silver catalyst contained about 12% by weight of silver.

Alkali metal promoters were added to this catalyst in the following way:

Appropriate quantities of alkali metal nitrates were dissolved in the minimum anoint of water required to give complete dissolution. The volume of this solution was made up to 5 ml by the addition of ethanol. This solution was then used to impregnate 25 g of the unpromoted catalyst and the resulting damp solid was dried in nitrogen in a forced draught oven for a period of 1 hour at a temperature of 120° C. The quantities of alkali metal contained in the resulting promoted catalysts are given in Table 3.

EXAMPLE 7

Catalysts 13–19 for the oxidation of ethylene to ethylene oxide were prepared as follows:

17.3 g of silver oxalate, prepared by the method described in Example 5, were dissolved in 39 ml of a 50:50 v/v solution of ethylene diamine in water. To this solution 3.9 ml of ethanolamine were added. 30 g of the support material was stirred into the silver solution and the mixture left to stand for about 10 mins. The excess solution was drained from the support and the resultant damp solid was heated in nitrogen at 200° C. for 1 hour in a forced draught oven. The support used was supplied by Carborundum. It was an alpha-alumina composite which had been crushed and sieved to give particles with diameters in the range 0.42 to 1 mm. The surface area of the support material was 0.56 m²/g, the mean pore diameter was 2.3 microns and the water porosity was 50%. This silver catalyst contained about 15% silver by weight.

Alkali metal promoters were added to this catalyst using the method described in Example 6. The quantities of alkali metal present on the final catalysts are given in Table 3.

EXAMPLE 8

Catalysts 20-26 for the oxidation of ethylene to ethylene oxide were prepared using an identical technique to that described in Example 7. The support used was an alpha-alumina composite sold by Norton Co. Before use it was crushed and sieved to give pellets 0.42 to 1 mm diameter. The surface area of the support material was 1.8 m²/g with a mean pore diameter of 1.2 microns and a water porosity of 50%. The catalysts contained about 15% silver by weight. The quantities of alkali metal promoters present are given in Table 3.

EXAMPLE 9

Catalysts 1-8, prepared in Example 5, were tested in the following way:

10 g of catalyst was loaded into a stainless steel reactor (internal diameter 8 mm). The catalyst was heated up to 170° C. in the presence of a process gas stream containing 30% ethylene, 8% oxygen, 62% nitrogen, 10 ppm vinyl chloride and 2 ppm nitric oxide. The process gas pressure was 225 p.s.i.g.

The temperature was slowly raised to 240° C. and the selectivity and oxygen conversion were measured at a gas hourly space velocity of 6000 hr⁻¹. The results are shown in Table 2.

EXAMPLE 10

Catalysts 9, 10, 15 and 20-25 were tested for activity in the following way:

10 g of catalyst were loaded into a stainless steel reactor (internal diameter 8 mm). A process gas stream containing 30% ethylene, 8% oxygen, 62% nitrogen end low levels of vinyl chloride and nitric oxide was passed through the reactor at a pressure of 225 p.s.i.g. The catalyst was heated rapidly to 170° C. and then more slowly to a temperature in the range 215-240° C. The vinyl chloride and nitric oxide levels and the gas hourly space velocity were adjusted over a period of 1-2 weeks until the optimum selectivity had been achieved with an oxygen conversion in the range 10-20%. The catalyst selectivities achieved under these conditions are given in Table 3.

EXAMPLE 11

Catalysts 11-14, 16-19 and 26 were tested for catalytic activity by the following method:

0.5 g of catalyst was loaded into a stainless steel reactor (internal diameter 2.0 mm). A process gas stream containing 30% ethylene, 8% oxygen, 62% nitrogen and a few ppm of vinyl chloride and nitric oxide was passed over the catalyst. The temperature of the catalyst was rapidly raised to 170° C. and then more slowly raised to 240° C. The vinyl chloride and nitric oxide levels and the gas hourly space velocity were adjusted as in Example 10 to achieve the optimum catalyst selectivity at an oxygen conversion in the range 10-20%. The results are given in Table 3.

TABLE 3

| Catalyst No | Na (ppm) | K (ppm) | Rb (ppm) | Cs (ppm) | Temp (°C.) | Vinyl Chloride (ppm) | Nitric Oxide (ppm) | GHSV (hr⁻¹) | Selectivity % | Oxygen Conversion % |
|---|---|---|---|---|---|---|---|---|---|---|
| 9 | 300 | — | 100 | — | 240 | 10.0 | 2.0 | 5300 | 88 | 13 |
| 10 | — | 300 | — | — | 224 | 6.5 | 1.0 | 6000 | 90 | 12 |
| 11 | — | 300 | 100 | — | 240 | 7.0 | 1.0 | 6200 | 89 | 12 |
| 12 | — | 1000 | 100 | — | 240 | 7.5 | 0.5 | 4600 | 90 | 10 |
| 13 | 50 | — | 600 | — | 240 | 8.0 | 2.0 | 7200 | 86 | 19 |
| 14 | 300 | — | 600 | — | 240 | 9.0 | 1.0 | 6400 | 88 | 14 |
| 15 | 300 | — | 750 | — | 240 | 10.0 | 1.0 | 4000 | 90 | 15 |
| 16 | — | 1000 | — | — | 240 | 7.5 | 0.5 | 5400 | 87 | 14 |
| 17 | 300 | — | — | 600 | 240 | 9.0 | 1.0 | 6000 | 88 | 12 |
| 18 | — | 1000 | — | 200 | 240 | 10.0 | 0.9 | 5400 | 89 | 13 |
| 19 | — | 1000 | — | 600 | 240 | 10.0 | 0.9 | 5400 | 89 | 13 |
| 20 | — | 1000 | — | — | 215 | 2.0 | 0.7 | 8000 | 89 | 13 |
| 21 | — | 1000 | 300 | — | 215 | 2.0 | 0.7 | 8000 | 91 | 12 |
| 22 | — | 1000 | 1000 | — | 215 | 2.0 | 0.7 | 8000 | 90 | 10 |
| 23 | — | 1000 | 3000 | — | 215 | 2.0 | 0.7 | 8000 | 91 | 9 |
| 24 | — | 2000 | 300 | — | 220 | 4.0 | 1.5 | 6700 | 92 | 16 |
| 25 | — | 600 | 300 | — | 220 | 10.0 | 1.0 | 6700 | 89 | 15 |
| 26 | — | 1000 | 300 | — | 230 | 6.0 | 1.4 | 6500 | 89 | 11 |

TABLE 2

| Catalyst | Na loading ppm | Rb loading ppm | Selectivity % | Oxygen Conversion % |
|---|---|---|---|---|
| 1 | 300 | 200 | 86 | 17 |
| 2 | 600 | 200 | 90 | 11 |
| 3 | 50 | 300 | 85 | 27 |
| 4 | 200 | 300 | 90 | 12 |
| 5 | 300 | 300 | 90 | 6 |
| 6 | 600 | 300 | 91 | 7 |
| 7 | 300 | 500 | 88 | 19 |
| 8 | 600 | 500 | 88 | 9 |

EXAMPLE 12

Catalysts 27-30 for the oxidation of ethylene to ethylene oxide were prepared as follows:

30 g silver acetate were dissolved in 30 ml of ammonia solution (specific gravity 0.880). The solution was filtered and 18 ml of water were added to the filtrate. This solution was used to impregnate 180 g of the support material. The support material used was an α-alumina composite sold by Norton Co. which had previously been washed and sieved to give particles with diameters in the range 0.42-1 mm. The surface area of the support was 0.3 m²/g, the mean pore diameter was 2.8 microns and the water porosity was 20%. The support impregnated with the silver acetate solution was heated in a forced draught oven for 3 hours at 290° C. This procedure resulted in a catalyst containing about 8% silver by weight.

Four 22 g portions of this silver catalyst were impregnated with 5.9 ml of solutions of cadmium nitrate in water. The impregnated catalysts were then heated for 1 hour at 290° C. in a forced draught oven. The levels of cadmium, expressed in parts per million by weight of catalyst, present on catalysts 27–30 are given in Table 4.

EXAMPLE 13

Catalysts 27–30 were tested for catalytic activity by the following method.

20 g of catalyst was loaded into a glass reactor tube (internal diameter 8 mm) immersed in a thermostatically controlled air bath. A process gas containing 30% ethylene, 8% oxygen, 62% nitrogen and 20 ppm vinyl chloride was introduced at a pressure of 5 p.s.i.g. The temperature of the reactor was raised to 240° C. and the selectivity to ethylene oxide and oxygen conversion over the catalyst were measured at a gas hourly space velocity of 400 $hr^{-1}$. The results are given in Table 4A.

10 ppm of nitric oxide was then included in the process gas stream in addition to the ethylene, oxygen and vinyl chloride. Once the catalyst performance had stabilised the selectivity to ethylene oxide and oxygen conversion were again measured. The results are given in Table 4B.

1 hour at a temperature of 200° C. The resulting supported silver catalyst contained about 6% silver.

Catalyst 31 was prepared by impregnating 25 g of this unpromoted catalyst with 5 ml of a solution of sodium carbonate in water. The resulting solid was then dried at 120° C. for 1 hour under nitrogen in a forced draught oven. This catalyst contained 300 ppm of sodium by weight in the form of sodium carbonate.

Catalyst 32 was prepared by the same method used for catalyst 31 but the catalyst contained 300 ppm of potassium by weight in the form of potassium acetate.

EXAMPLE 15

Catalysts 31 and 32 were tested in the following way:

6 g of catalyst was loaded into a stainless steel reactor (internal diameter 8 mm) and a process gas stream containing 30% ethylene, 8% oxygen and 20 ppm vinyl chloride was passed through the reactor at atmospheric pressure. The temperature of the reactor was raised to 224° C. and the selectivity and oxygen conversion measured at a GHSV of 330 $hr^{-1}$ once the catalyst performance had stabilised. A nitrate forming substance was then introduced into the process gas stream and the selectivity and oxygen conversion determined once a stable performance had been re-established. The nitrate forming substance was then removed and the catalyst selectivity and oxygen conversion determined again. The results are given in Table 5.

TABLE 4

| Catalyst | Cadmium content (ppm) | A In the absence of NO | | B In the presence of NO | |
|---|---|---|---|---|---|
| | | Selectivity % | Oxygen Conversion % | Selectivity % | Oxygen Conversion % |
| 27 | 30 | 86 | 8 | 91 | 8 |
| 28 | 100 | 85 | 8 | 89 | 8 |
| 29 | 300 | 83 | 7 | 89 | 4 |
| 30 | 1000 | 83 | 7 | 88 | 4 |

TABLE 5

| | | | PERFORMANCE | | | |
|---|---|---|---|---|---|---|
| | | | With Additive | | After Additive Removal | |
| | N-containing Additive | | | Oxygen | | Oxygen |
| Catalyst No | Type | Concentration (ppm) | Selectivity % | Conversion % | Selectivity % | Conversion % |
| 31 | — | No additive | 82 | 20 | — | — |
| 31 | NO | 20 | 85 | 18 | 86 | 17 |
| 31 | $NO_2$ | 20 | 87 | 9 | 91 | 13 |
| 31 | $NH_3$ | 150 | 88 | 15 | 89 | 18 |
| 31 | $C_2H_4(NH_2)_2$ | 70 | 86 | 15 | 86 | 15 |
| 32 | — | No additive | 80 | 29 | — | — |
| 32 | NO | 10 | 92 | 5 | 90 | 16 |
| 32 | $NO_2$ | 10 | 91 | 5 | 92 | 12 |
| 32 | $NH_3$ | 150 | 92 | 6 | 91 | 6 |
| 32 | $C_2H_4(NH_2)_2$ | 40 | 90 | 8 | 93 | 19 |
| 32 | $CH_3CN$ | 20 | 89 | 5 | 87 | 16 |

EXAMPLE 14

Catalysts 31 and 32 for the oxidation of ethylene to ethylene-oxide were prepared by the following method:

3.1 g of silver oxalate, prepared by the method described in Example 5, were dissolved in 5.4 ml of a 50:50 solution of ethylene diamine in water. To this solution 0.6 ml of ethanolamine were added. This solution was used to impregnate 30 g of the support material described in Example 6. The resulting material was heated under nitrogen in a forced draught oven for a period of

EXAMPLE 16

Catalysts 33 and 34 for the oxidation of propylene to propylene oxide were prepared as follows:

3.1 g of silver oxalate, prepared as in Example 5, were dissolved in 5.4 ml of a 50:50 v/v solution of ethylene diamine in water. To this solution 0.6 ml of ethanolamine was added. This solution was used to impregnate 30 g of the support material used in Example 6. The resulting damp solid was then heated under nitrogen in a forced draught oven for a period of 1 hour at a temperature of 200° C. Suitable amounts of sodium carbonate & ammonium molybdate were dissolved in 5 ml water and the solution used to impregnate the catalyst. The resulting solid was dried at 120° C. in nitrogen for a period of 1 hour. Catalyst 33 was analysed to contain about 8% silver, 0.3% sodium and 100 ppm molybdenum by weight. Catalyst 34 was analysed to contain about 8% silver, 0.3% sodium and 300 ppm molybdenum by weight.

EXAMPLE 17

Catalysts 33 and 34 were tested for activity towards propylene oxidation in the following way:

6 g of catalyst was loaded into a stainless steel reactor (internal diameter 8 mm) and a process gas stream containing 30% propylene, 8% oxygen and 1150 ppm dichloromethane was passed through the reactor at atmospheric pressure. The reactor temperature was raised to 240° C. and the selectivity to propylene oxide and the oxygen conversion were measured at a GHSV of 330 $hr^{-1}$ once the performance had stabilised. Nitric oxide was then introduced into the process gas stream at a level of 5000 ppm for a period of 17 hours. The nitric oxide was then removed and the catalyst selectivity and oxygen conversion determined again. The results of the tests on catalysts 33 and 34 are given in Table 6.

TABLE 6

| Catalyst | Initial Performance | | Performance after NO treatment | |
|---|---|---|---|---|
| | Selectivity % | Oxygen Conversion % | Selectivity % | Oxygen Conversion % |
| 33 | 14 | 12 | 18 | 12 |
| 34 | 35 | 6 | 40 | 8 |

EXAMPLE 18

Catalyst 35 for the oxidation of ethylene to ethylene oxide was prepared and tested as follows:

Five 30 g batches of catalyst, prepared using an identical method to that used for catalyst 16 (Example 7), were mixed together. The catalyst contained about 8% silver by weight and 1000 ppm by weight of potassium.

Catalyst 35 was tested for oxidation activity in the following way:

150 g of catalyst 35 was loaded into a stainless steel reactor 1.1 cm in diameter. The length of the catalyst bed was 100 cm. A gas stream containing 30% ethylene, 8% oxygen, 62% nitrogen, 7–5 ppm vinyl chloride and 1.5 ppm nitric oxide was introduced at a pressure of 225 p.s.i.g. The catalyst was heated rapidly to 165° C. and then more slowly to 240° C. At a gas hourly space velocity of 5300 $hr^{-1}$ the catalyst selectivity to ethylene oxide was 91% with an oxygen conversion of 25%.

EXAMPLE 19

Catalysts 36 and 37 for the oxidation of ethylene to ethylene oxide were prepared in the following way:

10.4 g of reagent grade silver acetate were dissolved in the minimum amount of ammonia solution required to give complete dissolution. This solution was then filtered and the filtrate made up to 12 ml with water. A support material, an alpha-alumina composite sold by Norton Co. under the trade mark ALUNDUM, was impregnated with the silver solution. The surface area of the support material was 0.3 m²/g, the mean pore diameter was 2.8 microns and the water porosity was 20%. The support was in the form of particles with diameters in the range 0.42–1 mm. The support impregnated with the silver solution was heated in a forced draught oven at 290° C. for a period of 3 hours in an atmosphere containing 10% oxygen in nitrogen. This procedure results in a catalyst containing about 8% silver by weight. The catalyst was then promoted with alkaline earth metal nitrates by the following technique.

Appropriate amounts of strontium or barium nitrate were dissolved in 4 ml of water. This solution was used to impregnate 20 g of the supported silver catalyst. The impregnated catalyst was then dried at 290° C. for a period of 3 hours in an atmosphere containing 10% oxygen and 90% nitrogen. Catalyst 36 contained about 100 ppm strontium and catalyst 37 contained 3000 ppm barium.

EXAMPLE 20

Catalysts 36 and 37 were tested for oxidation activity using the following method:

10 g of catalyst was loaded into a stainless steel reactor tube (internal diameter 8 mm). A process gas stream containing 30% ethylene, 8% oxygen, 62% nitrogen and 20 ppm of vinyl chloride at atmospheric pressure was passed through the reactor. The temperature of the reactor was raised to 240° C. and the stabilised selectivity to ethylene oxide and oxygen conversion were measured at a gas hourly space velocity of 800 $hr^{-1}$. The results are given in Table 7A. Nitric oxide was then introduced at a level of 12 parts per million for a period of 40 hours. The selectivity and oxygen conversion was then re-determined in the absence of nitric oxide at a gas hourly space velocity of 800 $hr^{-1}$. The results are given in Table 7B.

TABLE 7

| Catalyst | A Prior to NO Pulse | | B After NO Pulse | |
|---|---|---|---|---|
| | Selectivity % | Oxygen Conversion % | Selectivity % | Oxygen Conversion % |
| 36 | 83 | 5 | 86 | 6 |
| 37 | 82 | 12 | 86 | 13 |

EXAMPLE 21

Catalyst 38 for the oxidation of ethylene to ethylene oxide was prepared by the following method:

30 g of reagent grade silver acetate was dissolved in 30 ml of aqueous ammonia (S.G. 0.880) and the solution was filtered. 7.2 ml of a solution containing 8.9 g of sodium acetate in 20 ml distilled water and 3.6 ml of a solution containing 1.68 g rubidium carbonate in 250 ml distilled water were added to the silver solution. The resulting solution was used to impregnate 180 g of the support material described in Example 1.

The support impregnated with the silver solution was heated in a forced draught oven for a period of 4 hours in air. During this time the temperature was gradually increased from 100 ° C. to 300 ° C. The resulting catalyst contained about 8% silver, 3000 ppm sodium and 100 ppm rubidium all by weight.

EXAMPLE 22

Catalyst 38 was tested for oxidation activity by the following method:

6 g of catalyst was loaded into a stainless steel reactor (internal diameter 8 mm) and a process gas at 5 p.s.i.g. containing 30% ethylene, 8% oxygen, 62% nitrogen, 10 ppm vinyl chloride and 10 ppm nitric oxide was passed over the catalyst at 240° C. The selectivity and oxygen conversion were determined at a gas hourly space velocity of 700 hr$^{-1}$. The vinyl chloride in the process gas stream was then replaced by an alternative chlorocarbon moderator. The selectivity and oxygen conversion were then measured again using the same gas hourly space velocity. The results of these catalyst tests are shown in Table 8.

TABLE 8

| Catalyst No | Chlorocarbon Type | Level ppm | Selectivity % | Oxygen Conversion % |
|---|---|---|---|---|
| 38 | Vinyl chloride | 10 | 93 | 8 |
| 38 | Dichloroethane | 10 | 92 | 8 |
| 38 | Methyl chloride | 50 | 94 | 8 |
| 38 | 2-Chloropropane | 4 | 94 | 8 |

EXAMPLE 23

Catalyst 39 for the oxidation of ethylene to ethylene oxide was prepared as follows:

20 g of a commercial catalyst which had been used for the production of ethylene oxide for a period of 2 years was impregnated with 5 ml of an aqueous solution of sodium carbonate and rubidium carbonate. It was then dried in a forced draught oven for 1 hour at a temperature of 120° C. in an atmosphere containing 10% oxygen in nitrogen.

The catalyst was loaded into a stainless steel reactor (internal diameter 8 mm) and a process gas containing 30% ethylene, 8% oxygen, 62% nitrogen, 10 ppm vinyl chloride and 3 ppm nitric oxide at a pressure of 225 p.s.i.g. was passed over the catalyst. The temperature of the catalyst was slowly raised to 240° C. and once the performance had stabilised, a selectivity of 90% and an oxygen conversion of 5% was achieved using a gas hourly space velocity of 5000 hr$^{-1}$. In a comparative test the unalkalised catalyst was tested in the absence of nitric oxide. Otherwise the test conditions were identical. The selectivity was 83% at an oxygen conversion of 8%.

EXAMPLE 24

Catalyst 40 for the oxidation of ethylene to ethylene oxide was prepared as follows:

39.7 g of silver oxide were dissolved in 50 g of a solution of 87% lactic acid in water which was maintained at a temperature of 90°–95° C. 4 ml of a 30% solution of hydrogen peroxide was gradually added and the volume of the solution was made up to 95 ml by the addition of lactic acid. The yellow solution was decanted, at 95° C., and the volume made up to 100 ml by the addition of more lactic acid. 92 g of α-alumina support material was then added to the liquid. The surplus liquid was drained from the damp support pellets which were then transferred to an air purged oven and heated for 20 hours at 65° C. The oven temperature was slowly raised to 250° C. and held at this temperature for 4 hours. The resulting material was then ground and sieved to give particles with sizes in the range 0.42–1 mm. The support material used was supplied by Norton Co. under the trade mark ALUNDUM in the form of 8 mm diameter rings 8 mm long. The surface area was 0.3 m$^2$/g, the mean pore-diameter was 2.8 microns and the water porosity was 20%. The final material contained about 7% by weight of silver.

Appropriate amounts of sodium nitrate and rubidium nitrate were dissolved in the minimum amount of water required for complete dissolution and the volume of the solution was made up to 4 ml by the addition of ethanol. This solution was used to impregnate 20 g of the supported silver catalyst described above. The resulting material was dried in nitrogen for a period of 1 hour at 120° C. Catalyst 40 contained about 7% silver, 1000 ppm sodium and 100 ppm rubidium all by weight.

EXAMPLE 25

Catalyst 40 was tested for activity for ethylene oxidation using the following technique:

10 g of catalyst was loaded into a stainless steel reactor (internal diameter 8 mm) and a process gas stream containing 30% ethylene, 8% oxygen, 62% nitrogen, 10 ppm vinyl chloride and 2 ppm nitric oxide was passed over the catalyst at a pressure of 225 p.s.i.g. The reactor temperature was gradually raised to 240° C. and the gas hourly space velocity was adjusted to be 10,000 hr$^{-1}$. A selectivity to ethylene oxide of 90% was measured at an oxygen conversion of 12% once the performance of the catalyst had stabilised.

EXAMPLE 26

Catalysts 41 and 42 for the oxidation of ethylene to ethylene oxide were prepared using an identical method to that described in Example 8. The catalysts contained about 15% by weight of silver. Catalyst 41 contained 1000 ppm potassium and 300 ppm rubidium by weight and catalyst 42 contained 2000 ppm potassium and 300 ppm rubidium by weight.

EXAMPLE 27

Catalysts 41 and 42 were tested for oxidation activity using the following method:

15 g of catalyst was loaded into a stainless steel reactor tube (internal diameter 8 mm). A process gas stream containing 30% ethylene, 8% oxygen, 17 ppm vinyl chloride, 1.5 ppm nitric oxide, 0.6% ethane and 60 ppm propene with the remainder nitrogen was passed through the reactor at a pressure of 225 p.s.i.g. The temperature of the reactor was raised rapidly to 170° C. then more slowly to 220° C. Once the performance had stabilised catalyst 41 gave a selectivity of 89% while catalyst 42 gave a selectivity of 91% at oxygen conversion of 14% and with a gas hourly space velocity of 6700 hr$^{-1}$.

EXAMPLE 28

Catalyst 43 for the oxidation of ethylene to ethylene oxide was prepared ms follows:

12.6 g of barium hydroxide was dissolved in a 10% solution of formic acid in water. 0.34 g of rubidum carbonate were dissolved in the barium containing solution and 6 mls of this solution were used to impregnate 30 g of the alpha-alumina support material described in Example 1. The impregnated support material was heated in a forced draught oven in air for a period of 90 minutes at 300° C. 20 g of reagent grade silver acetate were dissolved in 20 ml of aqueous ammonia. The solution was filtered and 3 ml of ethanolamine was added to the filtrate together with 1.75 g of barium acetate. The pre-impregnated and pyrolysed support was then impregnated with 6 mls of the silver containing solution and the resulting solid was heated in air in a forced draught oven for a period of 4 hours. During this time the temperature was slowly raised from 100° to 300° C. The final catalyst contained about 8% silver, 1.2% barium and 500 ppm rubidium all by weight.

EXAMPLE 29

Catalyst 43 was tested using the following technique:

10 g of catalyst were loaded into a glass U-tube reactor (internal diameter 8 mm). A process gas stream at 5 psig containing 30% ethylene, 8% oxygen, 20 ppm vinyl chloride, 1 ppm nitric oxide and 62% nitrogen was passed over the catalyst at a temperature of 240° C. The gas hourly space velocity was 800 $hr^{-1}$. Under these conditions the measured selectivity to ethylene oxide was 95% at an oxygen conversion of 5%.

A 1 g sample of catalyst was immersed in 10 ml of distilled water for a period of 24 hours at room temperature. The nitrate level was then determined by a method which involved reaction with 2-4-xylenol in a strong sulphuric acid medium, followed by extraction of the resulting nitro-xylenol into toluene and then into aqueous sodium hydroxide. The nitrate level was then determined by measuring the optical density of the solution at a wavelength of 445 nm. Details of the method are given elsewhere (Anal. Chem. 21 1385 (1949).

The results obtained from unused and used samples of catalysts 44 and 45 are given in Table 9B.

TABLE 9A

| Catalyst | With NO/$O_2$ Treatment | | Without NO/$O_2$ Treatment | |
|---|---|---|---|---|
| | Selectivity % | Oxygen Conversion % | Selectivity % | Oxygen Conversion % |
| 44 | 95 | 3 | 85 | 3 |
| 45 | 95 | 2 | 86 | 3 |

TABLE 9B

| | Nitrate content (ppm) | | |
|---|---|---|---|
| Catalyst | Unused Catalyst (No NO/$O_2$ treatment) | Used with NO/$O_2$ pre-treatment | Used without NO/$O_2$ pre-treatment |
| 44 | 220 | 5900 | <100 |
| 45 | 850 | 5600 | <100 |

EXAMPLE 30

Catalysts 44 and 45 for the oxidation of ethylene to ethylene oxide were prepared by the following method:

10.4 g of reagent grade silver acetate was dissolved in the minimum amount of aqueous ammonia required to give complete dissolution. This solution gas filtered and made up to 12 ml with water. Appropriate amounts of sodium acetate were added to the solution at this stage. This solution was used to impregnate 60 g of the support material used in Example 1. The resulting solid was then dried in air for a period of 1 hour at a temperature of 120° C. Catalyst 44 contained about 8% silver and 1000 ppm of sodium by weight. Catalyst 45 contained 8% silver and 3000 ppm sodium by weight.

EXAMPLE 31

Catalysts 44 and 45 were tested for oxidation activity in the following way:

10 g of catalyst was loaded into a glass U-tube reactor. A gas stream containing 8% oxygen, 0.8% nitric oxide in helium at atmospheric pressure was passed over the catalyst for a period of 3 hours at a temperature of 240° C. The gas stream was then replaced with pure helium and the reactor cooled to room temperature. A process gas stream was then introduced which contained 30% ethylene, 8% oxygen, 62% helium and 20 ppm vinyl chloride at atmospheric pressure. The reactor temperature was rapidly raised to 240° C. and the selectivity and oxygen conversion were measured using a gas hourly space velocity of 1000 $hr^{-1}$. The results are shown in Table 9A.

A comparative experiment was also carried out under the same reaction conditions except that the catalysts were not subjected to the nitric oxide/oxygen pre-treatment. The selectivities and oxygen conversions achieved are also shown in Table 9A.

EXAMPLE 32

Samples of catalysts 44 and 45 prepared in Example 30 and tested in Example 31 were analysed for nitrate content in the following way:

EXAMPLE 33

Catalyst 46 for oxidation of ethylene to ethylene oxide was prepared as follows:

50 g of silver oxide was slowly added to 63 g of a solution of 87% lactic acid in water maintained at a temperature of 90°-95° C. 2.5 gm of a 30% hydrogen peroxide solution was slowly added followed by 2 g of a 44% solution of barium lactate in water. After the addition of a further 5 ml of lactic acid a clear yellow solution was obtained. This solution was used to impregnate 90 g of the support material. After 5 minutes the excess liquid was drained off and the resulting solid was heated for 20 hours at a temperature of 65° C. in a current of sir. The oven temperature was then increased gradually to 250° C. and then held at 250° C. for 4 hours. The support used for this catalyst was an alpha-alumina composite supplied by Norton Co. under the trade mark ALUNDUM in the form of 8 mm diameter spheres. The surface area was 0.4 $m^2$/g, the mean pore diameter was 7 microns and the water porosity was 36%.

This supported silver catalyst was ground and sieved to give particles with diameters in the range 0.42-1 mm. An appropriate quantity of potassium nitrate was dissolved in the minimum amount of water required to give complete dissolution. The volume of this solution was made up to 3.6 ml by the addition of ethanol. This solution was used to impregnate 10 g of the supported catalyst prepared above. The resulting solid was heated at a temperature of 120° C. in a nitrogen atmosphere for a period of 1 hour. Catalyst 46 contained about 16% silver, 5600 ppm barium and 1000 ppm potassium all by weight.

EXAMPLE 34

Catalyst 46 was tested using the following method:

10 g of catalyst was loaded into a glass U-tube reactor (internal diameter 8 mm). A process gas stream containing 30% ethylene, 8% oxygen, 62% nitrogen, 20 ppm vinyl chloride and I ppm nitric oxide was passed over the catalyst at atmospheric pressure. The temperature of the reactor was rapidly raised to 200° C. then more slowly raised to 240° C. The selectivity and oxygen conversion were determined at a gas hourly space velocity of 1000 hr$^{-1}$ after the catalyst performance had stabilised. The selectivity was 94% at an oxygen conversion of 7%.

In the above Examples the compositions of gas streams all given by volumes and the quantities of catalyst ingredients are given by weight.

GHSV means gas hourly space velocity reduced to 20° C. and atmospheric pressure.

p.s.i.g. means pounds per square inch gauge.

p.s.i.a. means pounds per square inch absolute.

We claim:

1. In a continuous process for the production of ethylene oxide which comprises contacting ethylene with oxygen in the presence of a silver-containing catalyst and from 1 to 50 parts per million by weight of vinyl chloride reaction modifier, the improvement which comprises continuously contacting the catalyst simultaneously with ethylene, oxygen and vinyl chloride modifier with a nitrogen oxide which is in the gas phase and which is in a concentration of 0.5 to 50 parts per million of $NO_2$ equivalent of the process gas by volume, said nitrogen oxide forming nitrate and or nitrite ions in the catalyst under process conditions, whereby the selectivity of the catalyst is maintained or increased or the rate of loss of selectivity is reduced.

2. A process according to claim 1 in which the silver-containing catalyst is alkali metal promoted.

3. A process according to claim 2 wherein the alkali metal is potassium.

4. A process as claimed in claim 1 in which the catalyst comprises 3 to 50% by weight of silver supported on a porous heat resisting support which has a surface area in the range 0.05 to 10 m$^2$/g as measured by the Brunauer Emmett and Teller method, an apparent porosity as measured by the mercury absorption method of at least 20% mean pore diameters of 0.1 to 20 microns as measured by the mercury porosimetry method and most of the silver judged in terms of numbers of silver particles is present in the form of discrete particles adhering to the support having equivalent diameters of less than 10,000 A.

5. A process as claimed in claim 1 in which the contacting is carried out at a temperature of 180° to 320° C. and at a partial pressure of 0.1 to 20 bars of oxygen.

* * * * *